US006214050B1

(12) United States Patent
Huene

(10) Patent No.: US 6,214,050 B1
(45) Date of Patent: Apr. 10, 2001

(54) EXPANDABLE IMPLANT FOR INTER-BONE STABILIZATION AND ADAPTED TO EXTRUDE OSTEOGENIC MATERIAL, AND A METHOD OF STABILIZING BONES WHILE EXTRUDING OSTEOGENIC MATERIAL

(76) Inventor: Donald R. Huene, 201 N. Valeria, Fresno, CA (US) 93701

(*) Notice: Subject to any disclaimer, the term of this patent is extended or adjusted under 35 U.S.C. 154(b) by 0 days.

(21) Appl. No.: 09/309,918

(22) Filed: May 11, 1999

(51) Int. Cl.[7] .......................................... A61F 2/44

(52) U.S. Cl. .......................................... 623/17.15

(58) Field of Search .......................... 623/17.11, 17.12, 623/17.13, 17.14, 17.15, 17.16; 606/61

(56) References Cited

U.S. PATENT DOCUMENTS

| | | | |
|---|---|---|---|
| Re. 34,293 | 6/1993 | Goble et al. | 623/13 |
| 2,100,570 | 11/1937 | Saleh | 72/105 |
| 2,562,419 | 7/1951 | Ferris | 81/55 |
| 3,846,846 | 11/1974 | Fischer | 3/1 |
| 4,011,602 | 3/1977 | Rybicki et al. | 3/1.9 |
| 4,262,665 | 4/1981 | Roalstad et al. | 128/92 |
| 4,447,915 | 5/1984 | Weber | 3/1.9 |
| 4,708,132 | 11/1987 | Silvestrini | 128/92 |
| 4,744,793 | 5/1988 | Parr et al. | 623/13 |
| 4,789,284 | 12/1988 | White | 411/50 |
| 4,870,957 | 10/1989 | Goble et al. | 128/92 |
| 4,963,144 | 10/1990 | Huene | 606/73 |
| 5,019,080 | 5/1991 | Herner | 606/73 |
| 5,026,373 | 6/1991 | Ray et al. | 606/61 |
| 5,037,422 | 8/1991 | Hayhurst | 606/72 |
| 5,059,193 | 10/1991 | Kuslich | 606/61 |
| 5,092,891 | 3/1992 | Kummer et al. | 623/16 |

(List continued on next page.)

FOREIGN PATENT DOCUMENTS

| | | |
|---|---|---|
| 1322067 | 2/1963 | (FR) . |
| 1368021 | 6/1964 | (FR) . |
| 343992 | 3/1931 | (GB) . |
| 662082 | 5/1979 | (SU) . |
| 1109142 | 8/1984 | (SU) . |

OTHER PUBLICATIONS

Ray Threaded Fusion Cage, Surgical Dynamics.

Surgical Technique, Anterior Approach, General Preparation, pp. 4–7.

MD–III Threaded Cortical Dowel, Design Rationale and Surgical Technique, Univ. of FL. Tissue Bank, Inc.

*Primary Examiner*—David J. Isabella
(74) *Attorney, Agent, or Firm*—Liniak, Berenato, Longacre & White, LLC

(57) ABSTRACT

An expandable implant is capable of extruding material during expansion. The expandable implant comprises an anchor structure and a movable structure. The anchor structure is adapted to be inserted at least partially into a bone or between two bones, and is adapted to be secured thereto by expansion. The movable structure is operatively connected to the anchor structure so that movement of the movable structure with respect to the anchor structure causes expansion of the implant and at least partial extrusion of material contained within the implant. Preferably, the implant also includes an actuation device which connects the anchor structure to the movable structure, and the material which is at least partially extruded is an osteogenic material. In response to mechanical manipulation, the actuation device can move the movable structure with respect to the anchor structure in a first predetermined direction which causes expansion of the implant and reduces the volume of a cavity within the implant. As a result of the reduction in volume, the osteogenic material is extruded at least partially out from the cavity. Also provided is a method of stabilizing first and second bones with respect to one another. The method comprises the steps of: inserting at least one expandable implant between the bones; expanding the implant; and extruding an osteogenic material from the implant during expansion thereof.

30 Claims, 2 Drawing Sheets

U.S. PATENT DOCUMENTS

| | | | |
|---|---|---|---|
| 5,094,563 | 3/1992 | Carletti | 403/194 |
| 5,129,902 | 7/1992 | Goble et al. | 606/65 |
| 5,161,916 | 11/1992 | White et al. | 405/259.6 |
| 5,171,278 | 12/1992 | Pisharodi | 623/17 |
| 5,176,682 | 1/1993 | Chow | 606/72 |
| 5,306,301 | 4/1994 | Graf et al. | 623/13 |
| 5,324,308 | 6/1994 | Pierce | 606/232 |
| 5,390,683 | 2/1995 | Pisharodi | 128/898 |
| 5,522,899 | 6/1996 | Michelson | 623/17 |
| 5,531,792 | 7/1996 | Huene | 623/16 |
| 5,593,409 | 1/1997 | Michelson | 606/61 |
| 5,609,635 | 3/1997 | Michelson | 623/17 |
| 5,645,589 | 7/1997 | Li | 623/16 |
| 5,653,762 | 8/1997 | Pisharodi | 623/17 |
| 5,658,335 | 8/1997 | Allen | 623/17 |
| 5,658,336 | 8/1997 | Pisharodi | 623/17 |
| 5,665,122 | 9/1997 | Kambin | 623/17 |
| 5,693,100 | 12/1997 | Pisharodi | 623/17 |
| 5,741,253 | 4/1998 | Michelson | 606/61 |
| 5,776,199 | 7/1998 | Michelson | 623/17 |
| 5,782,919 | 7/1998 | Zdeblick et al. | 623/17 |
| 5,785,710 | 7/1998 | Michelson | 606/61 |
| 5,800,550 | 9/1998 | Sertich | 623/17 |

EXPANDABLE IMPLANT FOR INTER-BONE STABILIZATION AND ADAPTED TO EXTRUDE OSTEOGENIC MATERIAL, AND A METHOD OF STABILIZING BONES WHILE EXTRUDING OSTEOGENIC MATERIAL

BACKGROUND OF THE INVENTION

The present invention relates to an expandable implant capable of providing inter-bone stabilization (e.g., intervertebral spinal stabilization) and also capable of extruding materials, such as osteogenic material, upon expansion. The present invention also relates to a method of stabilizing bones (e.g., spinal vertebrae) with respect to one another while extruding osteogenic material.

There are several situations where it becomes desirable to stabilize one bone with respect to another. One exemplary situation arises in patient's who suffer from chronic low back pain. Chronic low back pain is one of the most common and perplexing problems facing the field of orthopedic surgery. In addition to patient discomfort, chronic low back pain has several adverse societal impacts, including lost income and possible chronic dependence on drugs, alcohol and public relief programs.

In many cases, low back pain can be avoided by preventing relative motion between spinal vertebrae. This treatment is commonly referred to as intervertebral stabilization. To abate low back pain, stabilization is directed to stabilizing contiguous vertebrae in the lumbar region of the spine.

Surgical techniques are known for use in spinal stabilization. These techniques seek to rigidly join vertebrae which are separated by a degenerative disk. Ideally, the surgery effectively replaces the vertebra-disk-vertebra combination with a single rigid vertebra. Various surgical techniques have been developed which attempt to approach or approximate this ideal.

One technique known in the art is to partially remove a degenerated disk and insert a bone graft into the void formed by the removed disk. Other techniques involve use of a surgical prosthetic implant which, acting alone or in combination with bone fragments, replaces the use of bone grafts. Such implants have been provided in the form of an implant that is placed between two adjacent vertebrae. The implant may contain bone fragments to facilitate bone growth. The implant contacts adjacent vertebral plates and achieves vertebral fusion after a sufficient amount of bone growth occurs, thus treating or preventing back pain in patients that have discogenic pain.

While conventional implants can be filled with bone fragments to expedite bone growth, it is believed that the mere presence of the bone fragments is not enough to achieve the rate of bone growth that would be provided if the bone fragments or other osteogenic material were extruded from the implant. There is consequently a need for an expandable implant which is adapted to extrude osteogenic material during its expansion and which thereby is adapted to expedite the bone growth and fusion process. By expediting the bone growth and fusion process, it is possible to reduce the amount of time between surgery and the patient's ability to return to work or perform physically demanding activities.

There also is a need for an expandable implant which can be repositioned in the event that the stabilization provided by the initial positioning of the implant creates an undesirable vertebral alignment.

SUMMARY OF THE INVENTION

It is a primary object of the present invention to satisfy the foregoing needs by providing an expandable implant capable of extruding osteogenic material during expansion, to thereby expedite bone growth.

Another object of the present invention is to provide a method of stabilizing vertebrae with respect to one another while extruding osteogenic material.

Still another object of the present invention is to provide an expandable implant which can be contracted after expansion in order to facilitate repositioning of the implant.

To achieve these and other objects, the present invention provides an expandable implant comprising an anchor structure and a movable structure. The anchor structure is adapted to be inserted at least partially into a bone or between two bones, and is adapted to be secured thereto by expansion. The movable structure is operatively connected to the anchor structure so that movement of the movable structure with respect to the anchor structure causes expansion of the implant and at least partial extrusion of material contained within the implant.

Also provided is an expandable implant comprising an anchor structure, a movable structure, and an actuation device. The anchor structure is adapted to be inserted at least partially into a bone or between two bones, and is adapted to be secured thereto by expansion. The anchor structure has a cavity which contains osteogenic material. The movable structure delimits aspects of the cavity and is operatively connected to the anchor structure so that movement of the movable structure with respect to the anchor structure causes expansion of the implant and at least partial extrusion of the osteogenic material. The actuation device connects the anchor structure to the movable structure and is adapted to move, in response to mechanical manipulation, the movable structure with respect to the anchor structure in a first predetermined direction which causes expansion of the implant and reduces the volume of the cavity. As a result of the reduction in volume, the osteogenic material is extruded at least partially from the cavity.

The present invention also provides a method of stabilizing first and second bones with respect to one another. The method comprising the steps of inserting at least one expandable implant between the bones, expanding the implant, and extruding an osteogenic material from the implant during expansion thereof.

The above and other objects and advantages will become more readily apparent when reference is made to the following description taken in conjunction with the accompanying drawings.

DESCRIPTION OF THE PREFERRED EMBODIMENTS

Figure 1:
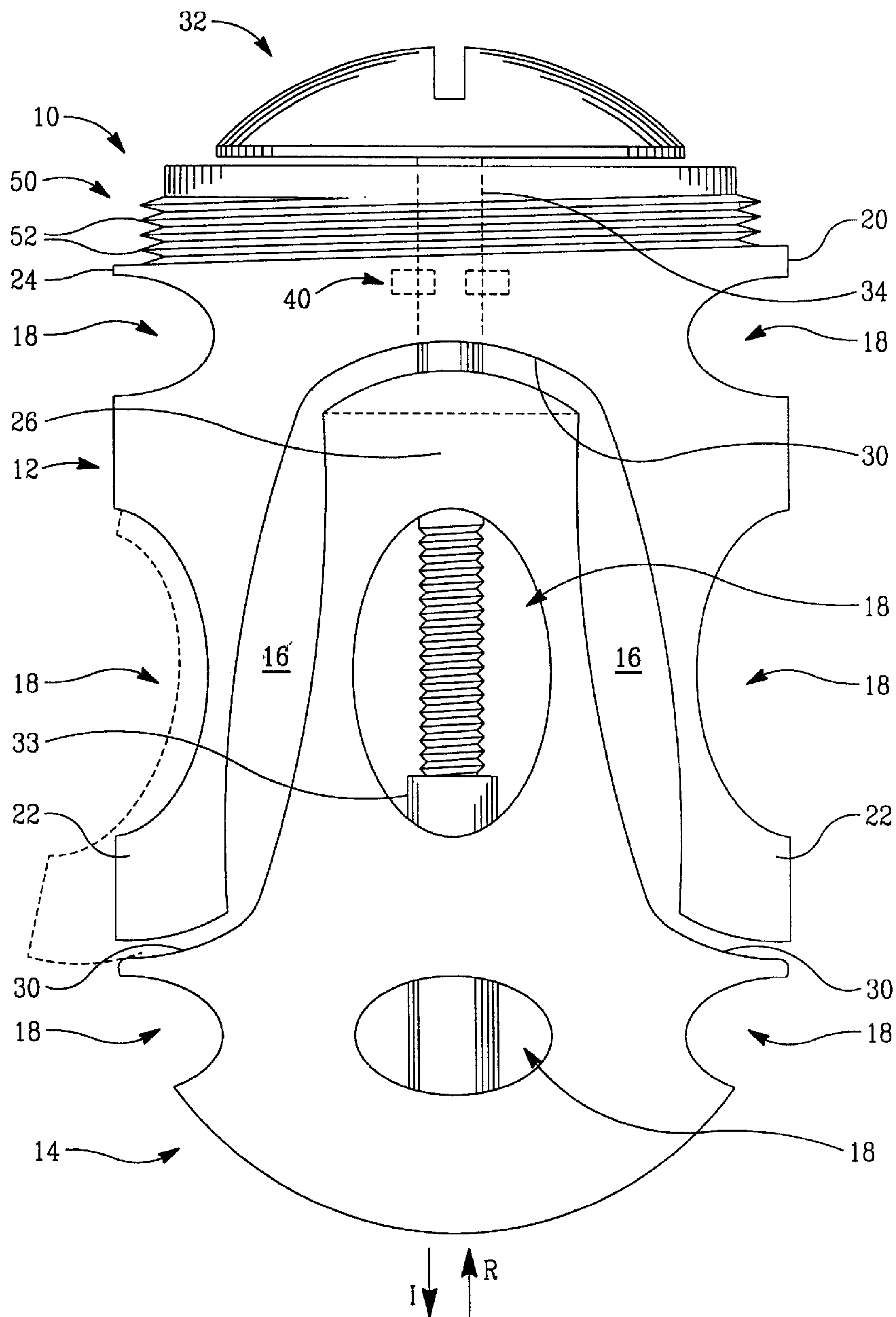
FIG. 1 is an elevation of an expandable implant according to a preferred embodiment of the present invention.

As best shown in FIG. 1, an expandable implant 10 according to a preferred embodiment of the present invention comprises an anchor structure 12 and a movable structure 14. The anchor structure 12 is adapted for insertion at least partially into a bone or between two bones and can be secured to the bone(s) by expansion. The expansion is achieved by moving the movable structure 14 with respect to the anchor structure 12. Such movement also advantageously causes at least partial extrusion of material contained within the implant.

In the exemplary embodiment, the anchor structure 12 and the movable structure 14 have shapes which cooperate to form a cavity 16 within the implant 10. The cavity 16 has a volume which varies depending upon the position of the movable structure 14 with respect to the anchor structure 12. The cavity 16 preferably is filled with an osteogenic material. The osteogenic material, for example, may include actual bone matter or any other substance capable of expediting or facilitating bone growth.

Preferably, the movable structure 14 and/or the anchor structure 12 has (or have) at least one extrusion opening 18. The extrusion opening(s) 18 provide access from the cavity 16 to an exterior of the implant 10. Preferably, both the movable structure 14 and the anchor structure 12 have a plurality of such extrusion openings 18, as illustrated in FIG. 1.

The anchor structure 12 also preferably includes a cap 20 and a plurality of fingers 22 extending axially from the cap 20. The plurality of fingers 22 preferably are located at the circumferential edge 24 of the cap 20. The plurality of fingers 22 are arranged with respect to one another and with respect to the cap 20 such that the cavity 16 is delimited by inside surfaces of the cap 20 and of the plurality of fingers 22. The cavity 16 also is delimited by an inside surface of the movable structure 14.

The movable structure 14 is movable at least partially through the cavity 16 to effect increases or reductions in the volume of the cavity 16 depending on the direction of movement. Arrow I in FIG. 1 denotes the direction of movement that increases the volume of the cavity 16, whereas arrow R denotes the direction of movement that causes the volume to be reduced. Preferably, as illustrated in FIG. 1, the movable structure 14 also includes fingers 26 (only one of which is visible in FIG. 1) which are interposed between the fingers 22 of the anchor structure 12. The fingers 26 of the movable structure 14 extend in the opposite axial direction as the fingers 22 of the anchor structure 12.

The exemplary implementation shown in FIG. 1 includes a total of four fingers 22,26 located symmetrically about the circumference of the implant 10. Each of the anchor structure 12 and movable structure 14 is associated with two of the fingers 22,26. The fingers 22,26 are centered about 90 degrees apart from one another along the circumference of the implant. The symmetrical arrangement, while not a limitation of the invention, is preferred regardless of the number of total fingers 22,26. Thus, six-finger embodiments preferably have fingers which are centered about 60 degrees from one another. Preferably, adjacent fingers 22,26 are spaced apart from one another to provide additional space through which the osteogenic material can be extruded.

Preferably, the movable structure 14 and the anchor structure 12 include bearing surfaces 30. The bearing surfaces 30 engage respective ones of the fingers 22,26 and urge the fingers 22,26 radially outward to effect expansion of the implant 10 when the movable structure 14 is moved in the direction denoted by arrow R.

The implant 10 also preferably includes an actuation device 32 adapted to move the movable structure 14 with respect to the anchor structure 12. While the illustrated exemplary embodiment uses a suitably configured bolt or screw as the actuation device 32, it is understood that the invention is not limited to such embodiments.

As illustrated in FIG. 1, the actuation device 32 connects the anchor structure 12 to the movable structure 14. In particular, the exemplary actuation device 32 passes through a hole 34 in the cap 20 of the anchor structure 12 and threadedly engages an internally threaded post 33 of the movable structure 14. Mechanical manipulation (e.g., rotation) of the actuation device 32 in a first predetermined direction causes the movable structure 14 to move toward the anchor structure 12 (i.e., toward the cap 20 of the anchor structure 12) in the direction denoted by arrow R. This movement serves to reduce the volume of the cavity 16 and thereby causes the osteogenic material or any other material contained within the cavity 16 to be at least partially extruded from the implant 10 (e.g., through the extrusion openings 18). The movement in the direction denoted by arrow R also causes the bearing surfaces 30 to urge the fingers 22,26 radially outward, and thereby effects expansion of the implant 10.

The broken lines in FIG. 1 show one of the fingers 22 in a radially outward position. Further movement of the movable structure 14 in the direction denoted by arrow R can cause the fingers 22 to extend radially out well beyond the exemplary position denoted by the broken lines.

Mechanical manipulation in a second predetermined direction (e.g., rotation in the opposite direction), by contrast, causes the movable structure 14 to move away from the cap 20 of the anchor structure 12 in the direction denoted by arrow I. Such movement in the direction denoted by arrow I causes radial contraction of the implant 10 as the force exerted by the bearing surfaces 30 on the fingers 22,26 diminishes. The resulting radial contraction of the implant 10 permits repositioning of the implant 10 should such repositioning become necessary or desirable after initial implantation.

Figure 2:
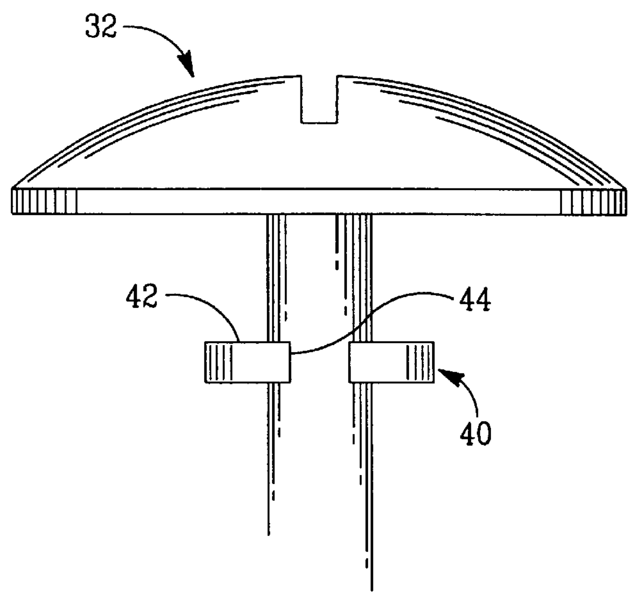
FIG. 2 is a cross-sectional view of an actuation device according to a preferred embodiment of the present invention.
Figure 3:
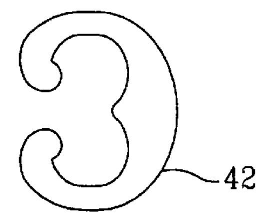
FIG. 3 is a plan view of a preferred embodiment of a clip for use in the actuation device illustrated in FIG. 2.

As illustrated in FIGS. 2 and 3, the actuation device 32 preferably includes a retention mechanism 40. The retention mechanism 40 includes a clip 42. The clip 42 is partially received in a circumferential notch 44 of the actuation device 32. When the clip 42 engages the notch 44, enough of the clip 42 extends out of the notch 44 to prevent the notched portion of the actuation device 32 from being withdrawn through the hole 34 in the anchor structure 12. The retention mechanism 40 thereby keeps the actuation device 32 from becoming separated from the anchor structure 12. While the preferred retention mechanism 40 uses the combination of the clip 42 and the notch 44, it is understood that the retention mechanism 40 can be implemented using alternative structures.

While various dimensions can be provided, depending on the intended use of each implant 10, a preferred implementation of the implant 10 includes dimensions that permit use of the implant 10 as an intervertebral stabilization device. The anchor structure 12 and movable structure 14, in this regard, are provided with dimensions that permit insertion of the expandable implant 10 between two vertebrae and expansion of the anchor structure 12 to provide stabilization of the two vertebrae with respect to one another. The exact dimensions will depend on the intervertebral spacing. In pediatric patients, the dimensions will be correspondingly smaller than the dimensions of an implant 10 that is intended for use with an adult patient. Exemplary dimensions for an adult spinal patient include an axial length of about 20 to 26 millimeters. The unexpanded diameter for the adult patient preferably is about 9 to 10 millimeters, with a diametric expansion of about 8 to 10 millimeters being provided by movement of the bearing surfaces 30 against the fingers 22,26.

As illustrated in FIG. 1, the cap 20 preferably is provided with a tool engagement feature 50. The exemplary tool engagement feature 50 comprises external threads 52. It is understood, however, that the invention is not limited to the exemplary feature, and that alternative structures can provide similar results.

An exemplary tool 60 which is capable of engaging the threads 52 for purposes of inserting or otherwise manipulating the implant 10, and which is also capable of turning the actuation device 32 to effect expansion or contraction of the implant 10 while remaining engaged to the threads 52, is disclosed in my U.S. Pat. No. 5,531,792. The contents of U.S. Pat. No. 5,531,792 are incorporated herein by reference.

Figure 4:
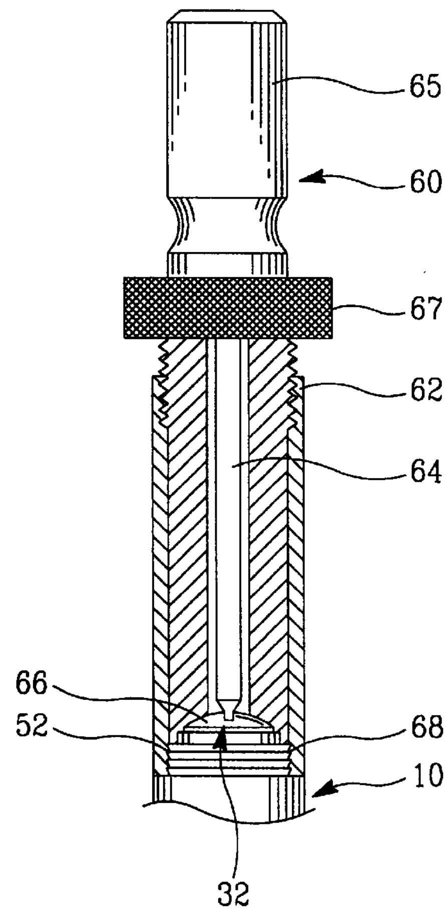
FIG. 4 is partial cross-sectional view of an exemplary tool that can be used in manipulating the expandable implant of the present invention.

As illustrated in FIG. 4, the tool 60 has a sleeve 62 which is internally threaded to engage the threads 52. A screw driver portion 64 passes through the sleeve 62 and engages the head 66 of the actuation device 32 to permit manual turning of the actuation device 32 while the sleeve 62 remains engaged to the threads 52. The sleeve 62 allows the entire implant 10 to be manipulated as a unit to achieve a desired position in the implant site, while the screw driver portion 64 facilitates movement of the movable structure 14 for purposes of selectively expanding or contracting the implant 10. The screw driver portion 64 preferably is connected to a screw driver handle 65 which provides a mechanical advantage when the screw driver portion 64 is turned. A knurled ring 67 is rigidly connected to the sleeve 62 to facilitate turning of the sleeve 62 with respect to the threads 52, for example, when connecting or disconnecting the tool 60 from the implant 10.

The movable structure 14, anchor structure 12, and actuation device 32 preferably are made of biocompatible material, such as surgical grade titanium or stainless steel. The osteogenic material preferably comprises bone material.

The implant 10 is particularly well-suited for use in stabilizing first and second bones with respect to one another. The implant 10 may be inserted into and/or between the bones after drilling or other appropriate preparation of the implantation site. Preferably, the insertion process includes threadedly connecting the threads 52 of the implant 10 to the internal threads 68 of the tool's sleeve 62, and using the tool 60 to insert the expandable implant 10 into the implantation site.

Once a desired position is achieved between the bones, the implant 10 can be expanded to tighten its engagement between the bones and/or prevent relative movement of the bones. This expansion preferably is accomplished by rotating the screw driver portion 64 of the tool 60 so that the actuation device 32 also rotates. During expansion, the osteogenic material is extruded from the implant 10, preferably through the extrusion openings 18 of the expandable implant 10. In particular, the extrusion is achieved by reducing the volume of the cavity 16 which holds the osteogenic material in each implant 10. The volume reduction is achieved by turning the actuation device 32 in the direction that causes the movable structure 14 to move in the direction of arrow R. The resulting extrusion during expansion advantageously expedites bone growth through the implant 10 and hastens the stabilizing effect provided thereby.

When stabilizing two vertebrae with respect to one another, for example, the stabilization method can be performed using two expandable implants 10 of the type described above. In particular, the steps of inserting, expanding, and extruding are performed between the two vertebrae.

After expansion of each implant 10, a determination can be made as to whether a desired alignment of the bones has been achieved and/or whether the relative position of the implant is appropriate. If this determination indicates that the desired relative alignment was not achieved, then one or both of the expandable implants 10 can be radially compressing (e.g., by turning the actuation device 32 in the direction that causes the movable structure 14 to move in the direction denoted by arrow I). The implant(s) 10 then can be repositioned and reexpanded. After reexpansion, the surgeon can verifying whether the desired relative alignment has been achieved. If this verification indicates that the desired relative alignment has not been achieved, the steps of radially compressing, repositioning, reexpanding, and verifying are repeated until the desired relative alignment is achieved.

Once the desired relative alignment is achieved, the knurled ring 67 can be rotated manually to disconnect the tool 60 from the threads 52 of the implant 10. It will be appreciated that the radial expansion provided by the implant 10 increases the frictional forces between the implant 10 and the implantation site and thereby serves to more positively retain the implant 10 in the implantation site. The additional frictional forces also advantageously keep the implant 10 from turning during removal of the tool 60 from the threads 52.

In treating some patients (e.g., scoleosis patients, patients with spinal curvature, and/or trauma patients), it may be desirable to connect the implant 10 to a spinal stabilization rod. Such rods are well known in the art.

Figure 5:
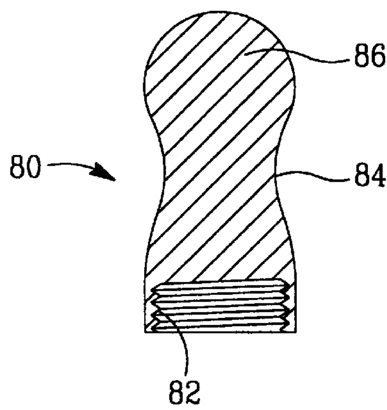
FIG. 5 is a cross-section view of an exemplary extension device that can be used to interconnect the implant and a spinal stabilization rod.

As shown in FIG. 5, the implant 10 can be provided with an implant extension 80. The exemplary implant extension 80 includes internal threads 82. The internal threads 82 are adapted to engage the threads 52 of the implant 10 and thus can be used to secure the extension 80 to the implant 10. The extension 80 further includes a neck portion 84 and a ball 86. The ball 86 and neck portion 84 can be engaged and locked to a suitable spinal stabilization rod in a trailer hitch-like manner. Alternatively, other engagement and locking means can be used to interconnect the rod and the implant 10.

While the expandable implant 10 and method are particularly well-suited for use in stabilizing vertebrae, it is understood that the invention is not limited to such use. The implant 10 can be modified and/or used to stabilize other bones, as one having ordinary skill in the art would readily appreciate from the instant disclosure.

Moreover, while this invention has been described as having a preferred design, it is understood that the invention is not limited to the illustrated and described features. To the contrary, the invention is capable of further modifications, usages, and/or adaptations following the general principles of the invention and therefore includes such departures from the present disclosure as come within known or customary practice in the art to which the invention pertains, and as may be applied to the central features set forth above, and which fall within the scope of the appended claims.

What is claimed is:

1. An expandable intervertebral implant comprising:

an anchor structure adapted to be inserted at least partially into vertebrae or between two vertebrae, and adapted to be secured thereto by expansion, said anchor structure having interiorly disposed surfaces and a plurality of radially movable fingers extending axially along said intervertebral implant;

a moveable structure having interiorly disposed surfaces and exteriorly disposed surfaces, said exteriorly disposed surfaces engageable with vertebrae, said movable structure being operatively connected to said anchor structure so that movement of said movable structure with respect to said anchor structure causes expansion of the implant and at least partial extrusion of material contained within the implant;

said anchor structure cooperating with said movable structure and defining a cavity delimited by said interiorly disposed surfaces of said anchor structure, said interiorly disposed surfaces of said movable structure, and said plurality of fingers; and at least one of said anchor structure and movable structure having an extrusion opening through which said at least partial extrusion of material in said cavity occurs.

2. The expandable intervertebral implant of claim 1, wherein said anchor structure and said movable structure have shapes which cooperate to form a cavity within said intervertebral implant, said cavity having a volume which varies depending upon positioning of said movable structure with respect to said anchor structure.

3. The expandable intervertebral implant of claim 2, wherein at least one of said movable structure and said anchor structure has at least one extrusion opening which provides access from said cavity to an exterior of said intervertebral implant.

4. The expandable intervertebral implant of claim 1, further comprising an actuation device adapted to move said movable structure with respect to said anchor structure, said actuation device having a first end threadedly connected to at least one of said anchor structure and said movable structure, said actuation device being responsive to torque applied in a first predetermined direction to cause said movable structure to move toward said anchor structure to produce radial expansion of the intervertebral implant and thereby at least partially extrude material contained within the implant.

5. The expandable intervertebral implant of claim 4, wherein said cavity has a volume which varies depending upon positioning of said movable structure with respect to said anchor structure.

6. The expandable intervertebral implant of claim 5, wherein said actuation device is responsive to torque in a second predetermined direction to cause said movable structure to move away from said anchor structure and provide radial contraction of said intervertebral implant.

7. The expandable intervertebral implant of claim 1, wherein an osteogenic material is contained in said cavity and is at least partially extruded during expansion.

8. The expandable intervertebral implant of claim 1, wherein said anchor structure includes a cap portion, said plurality of fingers extending axially from said cap portion; and wherein said movable structure is movable at least partially through said cavity to effect increases or reductions in a volume of said cavity depending on a direction of movement of said movable structure.

9. The expandable intervertebral implant of claim 8, wherein said movable structure includes bearing surfaces which engage respective ones of said plurality of fingers and urge said fingers radially outwardly to effect expansion of said intervertebral implant when said movable structure is moved in the direction which effects reductions in the volume of said cavity.

10. The expandable intervertebral implant of claim 8, wherein said movable structure also includes a plurality of fingers interposed between the plurality of fingers of said anchor structure, said anchor structure including bearing surfaces which engage respective ones of said plurality of fingers of the movable structure and urge said fingers of the movable structure radially outwardly to effect further expansion of said intervertebral implant when said movable structure is moved in the direction which effects reductions in the volume of said cavity.

11. The expandable intervertebral implant of claim 1, wherein said movable structure includes a plurality of fingers extending axially along said intervertebral implant, said plurality of fingers being arranged with respect to one another and with respect to said anchor structure such that a cavity is delimited by inside surfaces of said anchor structure and said plurality of fingers; and wherein said movable structure is movable at least partially through said cavity to effect increases or reductions in a volume of said cavity depending on a direction of movement of said movable structure.

12. The expandable intervertebral implant of claim 1, wherein each of said anchor structure and said movable structure has at least one extrusion opening.

13. The expanded intervertebral implant of claim 12, wherein an osteogenic material is contained within said cavity.

14. The expandable intervertebral implant of claim 1, wherein each of said anchor structure and said movable structure includes a plurality of extrusion openings.

15. The expandable intervertebral implant of claim 1, wherein said anchor structure and said movable structure have dimensions which permit insertion of said expandable intervertebral implant between two vertebrae and expansion of the anchor structure to provide stabilization of said two vertebrae with respect to one another.

16. An expandable intervertebral implant comprising:

an anchor structure adapted to be inserted at least partially into vertebrae or between two vertebrae, and adapted to be secured thereto by expansion, said anchor structure having interiorly disposed surfaces and a plurality of radially movable fingers extending axially along said intervertebral implant;

a movable structure having interiorly disposed surfaces and exteriorly disposed surfaces, said exteriorly disposed surfaces engageable with vertebrae, said movable structure operatively connected to said anchor structure so that movement of said movable structure with respect to said anchor structure causes expansion of the intervertebral implant and at least partial extrusion of osteogenic material from the implant;

said anchor structure cooperating with said movable structure and defining a cavity delimited by said interiorly disposed surfaces of said anchor structure, said interiorly disposed surfaces of said movable structure, and said plurality of fingers;

osteogenic material contained within said cavity;

an actuation device threadedly connected to at least one of said anchor structure and said movable structure and adapted to move, in response to torque, said movable structure with respect to said anchor structure in a first predetermined direction which reduces a volume of said cavity to thereby extrude said osteogenic material at least partially from said cavity and which causes expansion of said intervertebral implant; and at least one extrusion opening in at least one of said movable structure and anchor structure, through which said at least partial extrusion occurs.

17. The expandable intervertebral implant of claim 16, wherein said actuation device is responsive to torque in a second predetermined direction to cause said movable structure to move away from said anchor structure and provide radial contraction of said intervertebral implant.

18. The expandable intervertebral implant of claim 16, wherein each of said movable structure and said anchor structure has at least one extrusion opening which provides access from said cavity to an exterior of said intervertebral implant.

19. The expandable intervertebral implant of claim 16, wherein said anchor structure includes a cap portion, said plurality of fingers extending axially from said cap portion; and wherein said movable structure is movable at least partially through said cavity to effect increases or reductions in said volume depending on a direction of movement of said moveable structure.

20. The expandable intervertebral implant of claim 19, wherein said movable structure includes bearing surfaces which engage respective ones of said plurality of fingers and urge said fingers radially outwardly to effect expansion of said intervertebral implant when said movable structure is moved in the direction which effects reductions in the volume of said cavity.

21. The expandable intervertebral implant of claim 19, wherein said movable structure also includes a plurality of fingers interposed between the plurality of fingers of said anchor structure, said anchor structure including bearing surfaces which engage respective ones of said plurality of fingers of the movable structure and urge said fingers of the movable structure radially outwardly to effect further expansion of said intervertebral implant when said movable structure is moved in the direction which effects reductions in the volume of said cavity.

22. The expandable intervertebral implant of claim 16, wherein said movable structure is movable at least partially through said cavity to effect increases or reductions in a volume of said cavity depending on a direction of movement of said movable structure.

23. The expandable intervertebral implant of claim 16, wherein each of said anchor structure and said movable structure includes a plurality of extrusion openings.

24. The expandable intervertebral implant of claim 16, wherein said anchor structure and said movable structure have dimensions which permit insertion of said expandable intervertebral implant between two vertebrae and expansion of the anchor structure to provide stabilization of said two vertebrae with respect to one another.

25. A method of stabilizing first and second bones with respect to one another, said method comprising the steps of:

inserting at least one expandable implant between the bones, the implant having an anchor structure and a movable structure in operative connection and at least one extrusion opening, the anchor structure including an interiorly disposed surface and a plurality of radially movable fingers extending axially from the implant, the movable structure including an interiorly disposed surface, the anchor structure and the movable structure cooperating to form an internal cavity containing osteogenic material, the internal cavity delimited by the plurality of fingers and the interiorly disposed surfaces of the anchor structure and the interiorly disposed surfaces of the movable structure;

expanding the implant; and extruding the osteogenic material from the implant during expansion thereof.

26. The method of claim 25, wherein said step of inserting at least one expandable implant includes insertion of two expandable implants.

27. The method of claim 25, wherein said osteogenic material includes bone material.

28. The method of claim 25, wherein said steps of inserting, expanding, and extruding are performed between two vertebrae.

29. The method of claim 25, wherein said step of extruding is performed through the at least one extrusion opening (s) in said at least one expandable implant, by reducing a volume of the internal cavity.

30. The method of claim 25, further comprising the steps of:

determining whether a desired relative alignment of the first and second bones has been achieved after said step of expanding; and if said step of determining indicates that the desired relative alignment was not achieved, radially compressing said at least one expandable implant, repositioning said at least one expandable implant, reexpanding said at least one expandable implant, verifying whether the desired relative alignment has been achieved after repositioning and reexpansion, and if verification indicates that the desired relative alignment has not been achieved, repeating said steps of radially compressing, repositioning, reexpanding, and verifying until said desired relative alignment is achieved.

* * * * *